United States Patent [19]

Yamazaki

[11] Patent Number: 5,664,571
[45] Date of Patent: Sep. 9, 1997

[54] ULTRASONIC DIAGNOSTIC APPARATUS

[75] Inventor: Nobuo Yamazaki, Tokyo, Japan

[73] Assignee: Kabushiki Kaisha Toshiba, Kawasaki, Japan

[21] Appl. No.: 648,251

[22] Filed: May 15, 1996

[30] Foreign Application Priority Data

May 15, 1995 [JP] Japan ................... 7-115816

[51] Int. Cl.$^6$ .................................................. A61B 8/06
[52] U.S. Cl. .................... 128/660.05; 128/661.09
[58] Field of Search ................. 128/660.04, 660.05, 128/660.06, 660.07, 661.07–661.1

[56] References Cited

U.S. PATENT DOCUMENTS

| | | | |
|---|---|---|---|
| 5,170,792 | 12/1992 | Sturgill et al. | 128/660.05 X |
| 5,211,169 | 5/1993 | Freeland | 128/661.08 |
| 5,285,788 | 2/1994 | Arenson et al. | 128/660.05 |
| 5,474,073 | 12/1995 | Schwartz et al. | 128/916 X |

FOREIGN PATENT DOCUMENTS

| | | |
|---|---|---|
| 2-193650 | 7/1990 | Japan . |
| 6-114059 | 4/1994 | Japan . |

OTHER PUBLICATIONS

Ultrasound in Med. & Biol. vol. 18, Nos. 6/7, pp. 651–654, 1992; W. N. McDicken, et al. "Colour Doppler Velocity Imaging Of The Myocardium".

*Primary Examiner*—Francis Jaworski
*Attorney, Agent, or Firm*—Oblon, Spivak, McClelland, Maier & Neustadt, P.C.

[57] ABSTRACT

An ultrasonic wave transmitting/receiving portion transmits ultrasonic waves to a subject via an ultrasonic probe, then receives the ultrasonic waves reflected from the subject via the ultrasonic probe, and then converts the received ultrasonic waves into electric signals. A B-mode DSC portion converts the electric signals received by the ultrasonic wave transmitting/receiving portion into displaying signals. A Doppler signal processing portion detects Doppler signals from the electric signals supplied from the ultrasonic wave transmitting/receiving portion in terms of phase detection and analyzes both blood flow velocity and tissue motion velocity based on the Doppler signals within a processing time assigned to one scanning line. A displaying portion displays concurrently B-mode ultrasonic images supplied from the B-mode DSC portion and information as for blood flow velocity and tissue motion velocity supplied from the Doppler signal processing portion apparently.

19 Claims, 5 Drawing Sheets

ULTRASONIC DIAGNOSTIC APPARATUS

BACKGROUND OF THE INVENTION

1. Field of the Invention

The present invention relates to an ultrasonic diagnostic equipment and, more particularly, an ultrasonic diagnostic equipment for performing tissue Doppler imaging (TDI) in terms of ultrasonic-pulse Doppler technique.

2. Description of the Related Art

Conventionally, there has been an equipment recited in Patent Application Laid-open No. 6-114059 (entitled Ultrasonic Color Doppler Tomographic Equipment) as an ultrasonic diagnostic equipment for performing the tissue Doppler imaging. The ultrasonic diagnostic equipment is equipped with a mechanism which detects motion velocity of tissues of cardiac muscles and blood vessel walls using a low-pass filter in terms of the ultrasonic pulse Doppler technique, calculates a variety of physical quantity of motion based on the motion velocity, and displays the calculation results in color in an appropriate manner.

Color display of the calculation results may be carried out in various manners. In the above Laid-open Publication, two dimensional color display method has been disclosed. Blood flow imaging technique used in a color Doppler equipment which is established according to a principle common with the tissue Doppler imaging may be applied preferably to tone control in this color display.

In the foregoing blood flow imaging, images have been displayed in 32 tones ($f_r/32$ per tone), as shown in FIG. 9 of the above Publication, for example, by changing luminance or hue of color within the range where a Doppler deviation frequency $f_d$ is "$-f_r/2$ to $f_r/2$" (where $f_r$ a repetitive frequency of the ultrasonic pulse signal). In other words, tones in color display ranging from red (yellow) to blue (light blue) have been set by assigning such a scale that has uniform change in tone against the velocity (Doppler deviation frequency) to the throughout velocity range of "$-f_r/2$ to $f_r/2$".

Meanwhile, tissue motion as well as blood flow has been able to be monitored by the above ultrasonic diagnostic equipment. However, tissue motion and blood flow have not been analyzed concurrently, but they have been displayed selectively. But it is evident that, if tissue motion and blood flow can be displayed concurrently and analyzed simultaneously, more detailed diagnosis would be enabled by the ultrasonic diagnostic equipment. In particular, in the case of diagnosis of cardiopathy by the ultrasonic diagnostic equipment, it would be understood that detailed condition of the heart may be observed and grasped and therefore more precise and correct diagnosis may be pronounced if blood flow, cardiac muscle, and wall of blood vessel may be displayed concurrently and thus analyzed simultaneously.

SUMMARY OF THE INVENTION

The present invention has been made in view of the above circumstances, and it is an object of the present invention to provide an ultrasonic diagnostic equipment capable of analyzing and monitoring simultaneously blood flow and tissue motion apparently.

In order to achieve the above object of the present invention, there is provided an ultrasonic diagnostic equipment comprising: ultrasonic wave transmitting/receiving means for transmitting ultrasonic waves to a subject via an ultrasonic probe, receiving said ultrasonic waves reflected from the subject via the ultrasonic probe, and converting said ultrasonic waves into electric signals; B-mode ultrasonic image processing means for producing B-mode ultrasonic image information from the electric signals converted by the ultrasonic wave transmitting/receiving means; Doppler signal processing means for phase-detecting the electric signals supplied from said ultrasonic wave transmitting/receiving means to detect Doppler signals and analyzing both blood flow velocity and tissue motion velocity based on said Doppler signals within a processing time assigned to one scanning line; and displaying means for displaying B-mode ultrasonic images supplied from the B-mode ultrasonic image processing means and information as for the blood flow velocity and the tissue motion velocity supplied from the Doppler signal processing means.

According to the embodiment of the present invention, both blood flow velocity and tissue motion velocity may be analyzed within the process associated with one scanning based on the Doppler signals and may be simultaneously displayed apparently. As a result, conditions of region of interest can be grasped and thus diagnosis can be pronounced more precisely.

In the preferred embodiment of the present invention, the Doppler signal processing means analyzes the blood flow velocity and the tissue motion velocity in time-division way within a processing time assigned to one scanning line.

In the preferred embodiment of the present invention, the Doppler signal processing means analyzes the tissue motion velocity in the former half of processing time assigned to one scanning line and analyzes the blood flow velocity in the latter half of the processing time.

In the preferred embodiment of the present invention, the Doppler signal processing means comprises, phase detecting means for generating the Doppler signals, discriminating means for discriminating signals associated with tissue motion and signals associated with blood flow from the Doppler signals, and velocity information analyzing means for calculating the blood flow velocity or the tissue motion velocity based on the signals associated with tissue motion or the signals associated with blood flow.

In the preferred embodiment of the present invention, the discriminating means comprises, gain controlling means having a first level controlling means for effecting level adjustment so as to pass Doppler signals derived from blood flow and a second level controlling means for effecting level adjustment so as to remove said Doppler signal derived from said blood flow, filtering means for receiving the Doppler signal being level-adjusted by the first level controlling means to output an output signal after removing low frequency components of the Doppler signal, and signal selecting means for receiving the output signal from the filtering means and an output signal from the second level controlling means, and outputting them selectively.

In the preferred embodiment of the present invention, the velocity information analyzing means comprises, autocorrelation calculating means for receiving an output signal from the signal selecting means to calculate autocorrelation, and velocity calculating means for calculating the blood flow velocity or the tissue motion velocity based on calculation results of the autocorrelation calculating means.

In the preferred embodiment of the present invention, an ultrasonic diagnostic equipment, further comprises: switching controlling means for controlling of selection of output signals when the signal selecting means selectively outputs an output signal from the second level controlling means and an output signal from the filtering means, and for providing range and coefficient of autocorrelation calculation for an output signal of the second level controlling means, i.e., Doppler signals derived from tissue motion, and range and coefficient of autocorrelation calculation for an output signal of the high frequency filtering means, i.e., Doppler signals derived from blood flow, to the autocorrelation calculating means and the velocity calculating means upon controlling the selection.

In the preferred embodiment of the present invention, the Doppler signal processing means further comprises, digital scan converting means for storing information as for the blood flow velocity and the tissue motion velocity derived by process within the processing time assigned to one scanning line in a frame memory, and outputting the information simultaneously.

In the preferred embodiment of the present invention, the Doppler signal processing means further comprises, a coloring circuit for converting the information as to the blood flow velocity and the tissue motion velocity into color display data.

According to this embodiment of the present invention, calculation of autocorrelation and velocity can be executed by the autocorrelation calculating means and the velocity calculating means by virtue of switching the output signal of the filtering means and the output signal of the second level controlling means by the signal selecting means. As a result, tissue motion velocity and blood flow velocity may be derived respectively from a low frequency component and a high frequency component of the Doppler signals every process concerning to one scanning line. Thus, if tissue motion velocity and blood flow velocity which have thus been derived by simultaneous analysis every process associated with one scanning line are stored in different pages in the frame memory and then output simultaneously, they may be displayed simultaneously.

In addition, according to this embodiment of present invention, since autocorrelation and velocity as for the Doppler signals being passed through the high frequency filtering means are calculated in the latter half of the process concerning to one scanning line, calculations may be implemented without influence of unnecessary components which are included in the former half of the process concerning to one scanning line. Instead, since autocorrelation and velocity as for the Doppler signals from the level controller 26b, i.e., the Doppler signals derived from tissue motion, are calculated in the former half of the process concerning to one scanning line, tissue motion velocity and blood flow velocity may be obtained quickly in the end.

In the preferred embodiment of the present invention, the displaying means comprises memory synthesizing means for superposing the B-mode ultrasonic image and the information as to the blood flow velocity and the tissue motion velocity and storing resultant information.

In the preferred embodiment of the present invention, the memory synthesizing means stores selectively information of the tissue motion velocity and information of the blood flow velocity according to intensity of the Doppler signal pixel by pixel.

According to this embodiment of the present invention, blood flow velocity and tissue motion velocity may be displayed distinguishably by causing the memory synthesizing means to store selectively blood flow velocity and tissue motion velocity according to the Doppler signals.

In the preferred embodiment of the present invention, the memory synthesizing means stores selectively information of the tissue motion velocity and information of the blood flow velocity according to luminance of the B-mode ultrasonic image pixel by pixel.

According to this embodiment of the present invention, blood flow velocity and tissue motion velocity may be displayed distinguishably by causing the memory synthesizing means to store selectively blood flow velocity and tissue motion velocity according to luminance of the B-mode ultrasonic images.

In the preferred embodiment of the present invention, the displaying means has in parallel a screen on which information of the tissue motion velocity is displayed and a screen on which information of the blood flow velocity is displayed.

The nature, principle and utility of the invention will become more apparent from the following detailed description when read in conjunction with the accompanying drawings.

DESCRIPTION OF THE PREFERRED EMBODIMENT

There will now be explained an embodiment of an ultrasonic diagnostic equipment of the present invention hereinafter with reference to accompanying drawings.

According to this embodiment, an ultrasonic diagnostic equipment is a tissue Doppler imaging equipment for obtaining CDI (Color Doppler Imaging) images of cardiac muscle (cardiac wall) as an example of the tissue.

Figure 1:
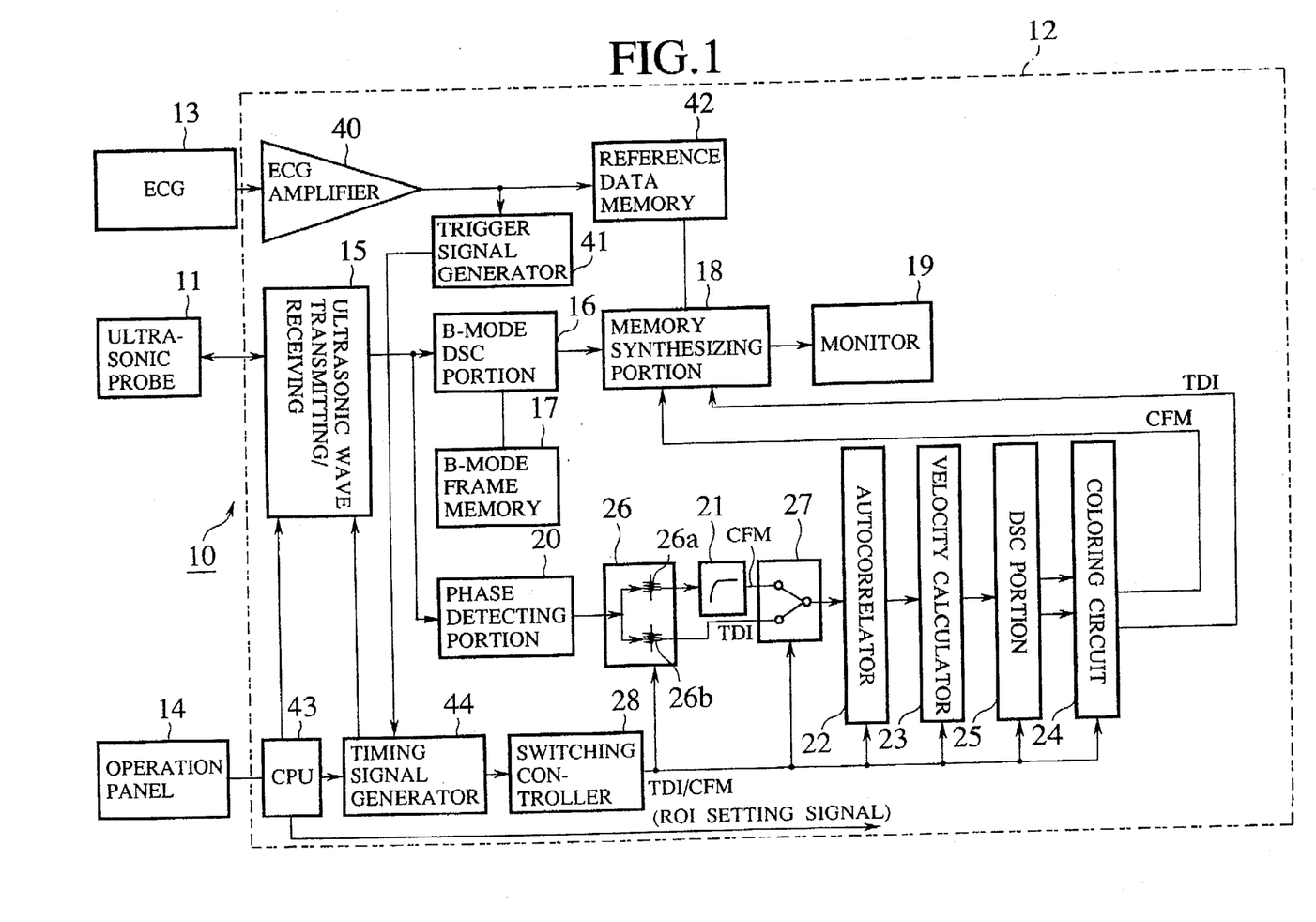
FIG. 1 is a block circuit diagram showing an embodiment of an ultrasonic diagnostic equipment according to the present invention.

FIG. 1 is a block circuit diagram showing a configuration of an ultrasonic diagnostic equipment according to the present invention. The ultrasonic diagnostic equipment 10 comprises an ultrasonic probe 11 for carrying out transmission/reception of ultrasonic signals between a subject and the ultrasonic diagnostic equipment, a main body 12 of the ultrasonic diagnostic equipment for driving the ultrasonic probe 11 and processing signals received by the ultrasonic probe 11, an ECG (ElectroCardioGraph) 13 connected to the main body 12 of the ultrasonic diagnostic equipment and for detecting electrocardiogram information, and an operation panel 14 connected to the main body 12 of the ultrasonic diagnostic equipment and for outputting instruction information from the operator to the main body of the ultrasonic diagnostic equipment.

The operation panel 14 is an input device for inputting operation information into a CPU (Central Processing Unit) 43. The CPU 43 may supplies a ROI (Region Of Interest) setting signal which is instructed by the operator via the operation panel 14 to respective concerning portions necessary for the ROI setting operation.

An ECG amplifier 40 is connected to the ECG 13. A trigger signal generator 41 and a reference data memory 42 are connected to an output terminal of the ECG amplifier 40. The reference data memory 42 receives ECG waveforms from the ECG 13 and stores electrocardiogram information in respective heartbeat phases, and then supplies necessary information to a memory synthesizing portion 18 if need be. The ECG waveforms are displayed as reference signals on a screen of a monitor 19 together with ultrasonic images. The trigger signal generator 41 detects R waves in ECG waveforms and supplies timing information in respective heartbeat phases to a timing signal generator 44.

The timing signal generator 44 is usually under control of the CPU 43 which controls delay time patterns in an ultrasonic wave transmitting/receiving portion 15 in response to the instruction from the operation panel 14, and supplies operation timing signals to respective portions of the equipment. When the timing signal generator 44 receives timing information in respective heartbeat phases from the trigger signal generator 41, it outputs a reference signal to transmit/receive the ultrasonic wave to the ultrasonic wave transmitting/receiving portion 15.

A switching controller 28 performs gain control of a gain controller 26 and in addition switching control of a signal selector 27. The switching controller 28 switches an operation range to be supplied to an autocorrelator 22 and a coefficient to be supplied to a velocity calculator 23 at the same time when the signal selector 27 is switched.

The ultrasonic probe 11 is connected to the ultrasonic wave transmitting/receiving portion 15. A B-mode DSC (digital scan converter) portion 16 and a B-mode frame memory (FM) 17 are arranged on the output side of the ultrasonic wave transmitting/receiving portion 15. B-mode ultrasonic images being input into the B-mode DSC portion 16 are stored in the frame memory 17 and are also displayed on the screen of the monitor 19 via the memory synthesizing portion 18. These portions are also mounted on the ultrasonic diagnostic equipment which has already been in practical use. Color display devices such as CRT may be used as the monitor 19.

Figure 2:
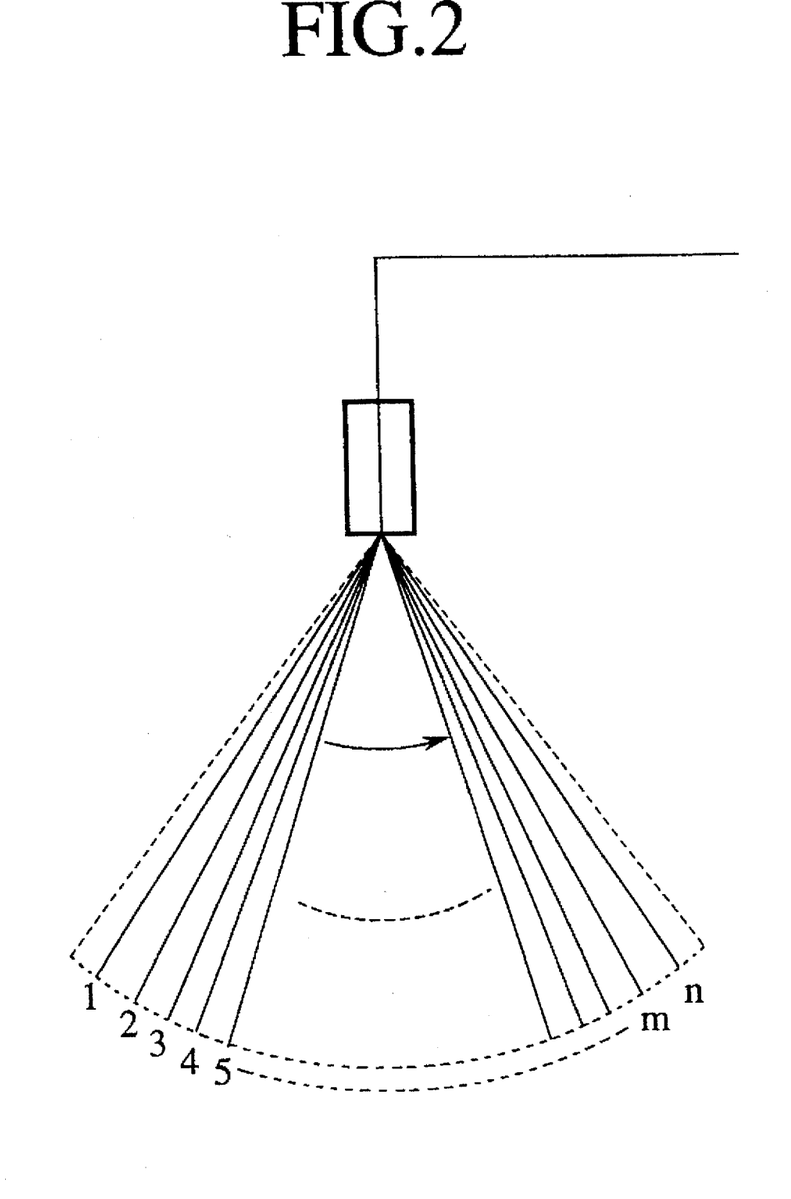
FIG. 2 is a view illustrating a method of scanning ultrasonic pulses.

A phased array type transducer in which a plurality of strip-like piezoelectric vibrators are arranged is built in the ultrasonic probe 11. Respective piezoelectric vibrators are excited by a driving signal supplied from the ultrasonic wave transmitting/receiving portion 1.5. If the scanning direction is shifted sequentially like scan 1, scan 2, scan 3, . . . , scan n, as shown in FIG. 2, by controlling delay time for respective driving signals, sector electron scanning can be achieved.

The ultrasonic wave transmitting/receiving portion 15 outputs to the ultrasonic probe 11 a driving voltage signal whose delay time pattern is controlled according to the scanning direction. When the ultrasonic probe 11 receives the driving voltage signal, it converts the driving voltage signal into the ultrasonic signal by the transducer therein. The converted ultrasonic signal is emitted to the heart and others of the subject. The emitted ultrasonic signal is reflected by respective tissues including the heart so as to return to the ultrasonic probe 11 again. The transducer provided in the probe 11 converts the reflected ultrasonic signal into a voltage signal (echo signal). The echo signal is then output from the ultrasonic wave transmitting/receiving portion 15.

A signal processing circuit provided in the ultrasonic wave transmitting/receiving portion 15 delays the input echo signal to permit a phasing addition of the echo signals like in the transmitting procedures, so that it generates an echo beam signal which is equivalent to the ultrasonic beam restricted in the scanning direction. The echo beam signals the phasing addition of which has been executed are detected and then output to the B-mode DSC portion 16. The DSC portion 16 extracts B-mode ultrasonic image data from echo data derived from the ultrasonic scanning, then converts them into standard TV scanning signals, and then outputs the scanning signals to the memory synthesizing portion 18. In addition, the B-mode DSC portion 16 lets the B-mode frame memory 17 store a plurality sheets of image data therein in arbitrary heartbeat phase.

The memory synthesizing portion 18 receives the B-mode ultrasonic images and CDI images described later and, if necessary, electrocardiogram information. These information are superposed and then displayed on the screen of the monitor 19. If multiple colors of the images are displayed overlappedly on the same pixels, such process is implemented in the memory synthesizing portion 18 that any color of the images may be preferentially displayed on the screen of the monitor 19 according to luminance of the B-mode images.

More particularly, in the event that blood flow information and tissue motion information are displayed simultaneously on the same pixels, the memory synthesizing portion 18 makes the monitor 19 display the tissue motion information when luminance of the B-mode images is greater than or equal to a threshold value Whereas the memory synthesizing portion 18 makes the monitor 19 display the blood flow information when luminance of the B-mode images is less than the threshold value. As another way of displaying the information, the memory synthesizing portion 18 may cause the monitor 19 to display the tissue motion information when the Doppler signal described later is greater than or equal to a threshold value, and on the contrary it may cause the monitor 19 to display the blood flow information when the Doppler signal is less than the threshold value.

A phase detecting portion 20 detects the echo signal supplied from the ultrasonic wave transmitting/receiving portion 15 by virtue of phase detection to detect the Doppler signal. The ultrasonic signals reflected by the moving areas are deviated according to the Doppler effect. Thus, beat frequencies are generated by the phase detection according to the Doppler deviation frequency. These beat frequencies serve as the echo signals.

The gain controller 26 is made up of a level controller 26a and a level controller 26b. The level controller 26a adjusts the level so as to pass the Doppler signals derived from blood flow while the level controller 26b adjusts the level so as to remove the Doppler signals derived from blood flow. The high-pass filter portion 21 passes high frequency components of the echo signals the level of which has been adjusted by the level controller 26a. The high-pass filter portion 21 operates in conformity with digital process installed in the ultrasonic diagnostic equipment which has already been put to practical use.

The signal selector 27 acts to switch the echo signals which are passed through the high-pass filter portion 21 (CFM and the echo signals which are level-controlled by the level controller 26b (TDI). A switching operation of the signal selector 27 is controlled by the switching controller 28.

The autocorrelator 22 calculates autocorrelation of the echo signal sent from the signal selector 27 and detects an average Doppler deviation frequency of respective echo signals. An average velocity near respective sample points defined in predetermined spaces, i.e., sample volumes in the ultrasonic wave transmitting/receiving portion 15 can be calculated by the autocorrelator 22 as velocity data in real time. A time interval for autocorrelation calculation can be switched and controlled by the switching controller 28. The velocity calculator 23 receives an analysis result of this Doppler frequency as color Doppler information relative to motion velocity.

The velocity calculator 23 has a CPU function, and therefore calculates blood flow velocity or tissue motion velocity based on the frequency distribution which has been calculated by the autocorrelator 22 in the preceding stage. The same procedures may be applied to calculate both blood flow velocity and tissue motion velocity, but different coefficients must be used in the velocity calculator 23 since the Doppler signals derived from respective blood flow and tissue motion are differently level-adjusted by the gain controller 26. The switching controller 28 performs the switching of the coefficients.

A CFM DSC portion 25 is provided to convert the scanning scheme. In particular, the DSC portion 25 converts velocity data which have been obtained from the ultrasonic scanning signals by the velocity calculator 23 into the standard TV scanning signals. The frame memory in the DSC portion 25 may store several tens of sheets of images in many pages which may be switched. Images of blood flow velocity and velocity data of tissue motion velocity may be stored respectively in different pages within the process assigned to one scanning line, while switching them by the switching controller 28. In addition, images of blood flow velocity and velocity data of tissue motion velocity may be read simultaneously from the DSC portion 25 to be output to the coloring circuit 24.

A look-up table is included in the coloring circuit 24, which colors velocity data supplied from the DSC portion 25 according to the magnitude of velocity with respect to blood flow velocity and tissue motion velocity. The coloring circuit 24 converts velocity data of respective blood flow velocity and tissue motion velocity into color display data, and then outputs the converted signal to the memory synthesizing portion 18. With changing their hues according to respective blood flow velocity information and tissue motion velocity information, the coloring circuit 24 converts velocity data into color display data. For instance, in accordance with setting up by the user, blood flow velocity information may be displayed in color while tissue motion velocity information may be displayed on the gray scale. Otherwise, blood flow velocity information may be displayed on the gray scale while tissue motion velocity information may be displayed in color.

Subsequently, an operation of the ultrasonic diagnostic equipment of the present invention will be explained.

Ultrasonic waves are transmitted from the ultrasonic probe 11 to the subject, and then reflected by tissues of the subject such as cardiac muscles, blood vessel walls, etc. Reflected ultrasonic waves are converted into voltage signals (echo signals) by the transducers in the ultrasonic probe 11. The echo signals are processed by the ultrasonic wave transmitting/receiving portion 15 and then stored as B-mode images in the frame memory 17 via the B-mode DSC portion 16. The B-mode images are output to the memory synthesizing portion 18 via the B-mode DSC portion 16, and are then superposed with CDI images and electrocardiograms to display on the screen of the monitor 19.

On the contrary, the echo signals supplied from the transmitting/receiving portion 15 are detected as Doppler signals by virtue of phase detection in the phase detecting portion 20 and then level-controlled by the gain controller 26. At this time, the level controller 26a adjusts the level so as to pass the Doppler signals derived from blood flow while the level controller 26b adjusts the level so as to remove the Doppler signals derived from blood flow. The Doppler signals which have been level-adjusted by the level controller 26a are input into the high-pass filter portion 21. The Doppler signals derived from blood flow are passed through the high-pass filter portion 21, but the low frequency Doppler signals derived from wall motion are removed by the high-pass filter portion 21. For this reason, output signals supplied from the level controllers 26a, 26b to the signal selector 27 may be discriminated respectively into the signals consisting of only the Doppler signal derived from blood flow and the signals consisting of only the Doppler signal derived from wall motion.

Figures 3A, 3B:
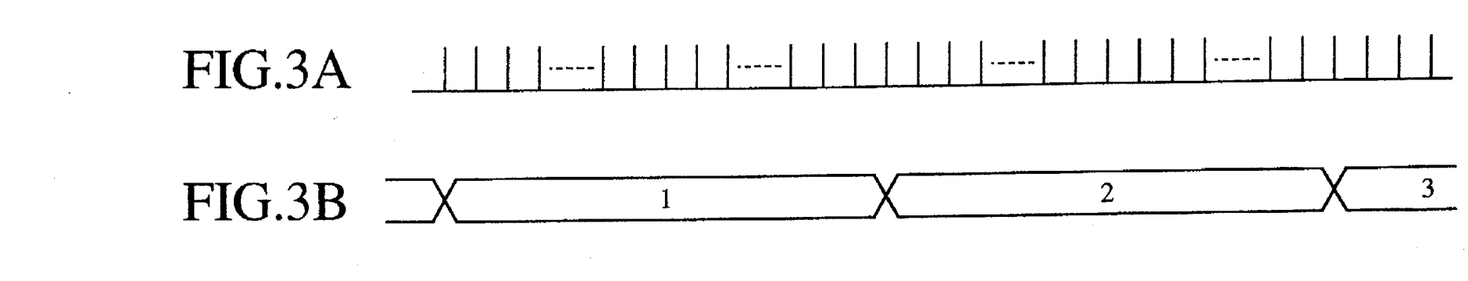
FIGS. 3A to 3E are timing charts showing respectively transmission/reception of ultrasonic wave, switching of a signal selector, echo signals not passed through a high-pass filter portion, echo signals passed through the high-pass filter portion, and calculation of autocorrelation and velocity.

In the meanwhile, transmission and reception of the ultrasonic waves are carried out several times between the subject and the ultrasonic diagnostic equipment relative to one scanning line. FIG. 3A shows rate pulses for transmission and reception of the ultrasonic waves, and FIG. 3B shows the scanning intervals. The switching controller 28 switches the signal selector 27 within the scanning assigned to one scanning line. Further, the switching controller 28 provides the echo signals which are not passed through the high-pass filter portion 21, i.e., the signals including only the Doppler signals derived from the wall motion, to the autocorrelator 22 in the former half of the scanning associated with one scanning line, and also provides the echo signals which have been passed through the high-pass filter portion 21, i.e., the signals including only the Doppler signals derived from the blood flow, to the autocorrelator 22 in the latter half of the scanning associated with one scanning line. Furthermore, the switching controller 28 provides a range and a coefficient used to calculate autocorrelation for tissue motion velocity to both the autocorrelator 22 and the velocity calculator 23 in the former half of the process concerning to one scanning line, and also provides a range and a coefficient used to calculate autocorrelation for blood flow velocity to both the autocorrelator 22 and the velocity calculator 23 in the latter half of the process concerning to one scanning line. Such operations are repeated every scanning line.

Figure 4:
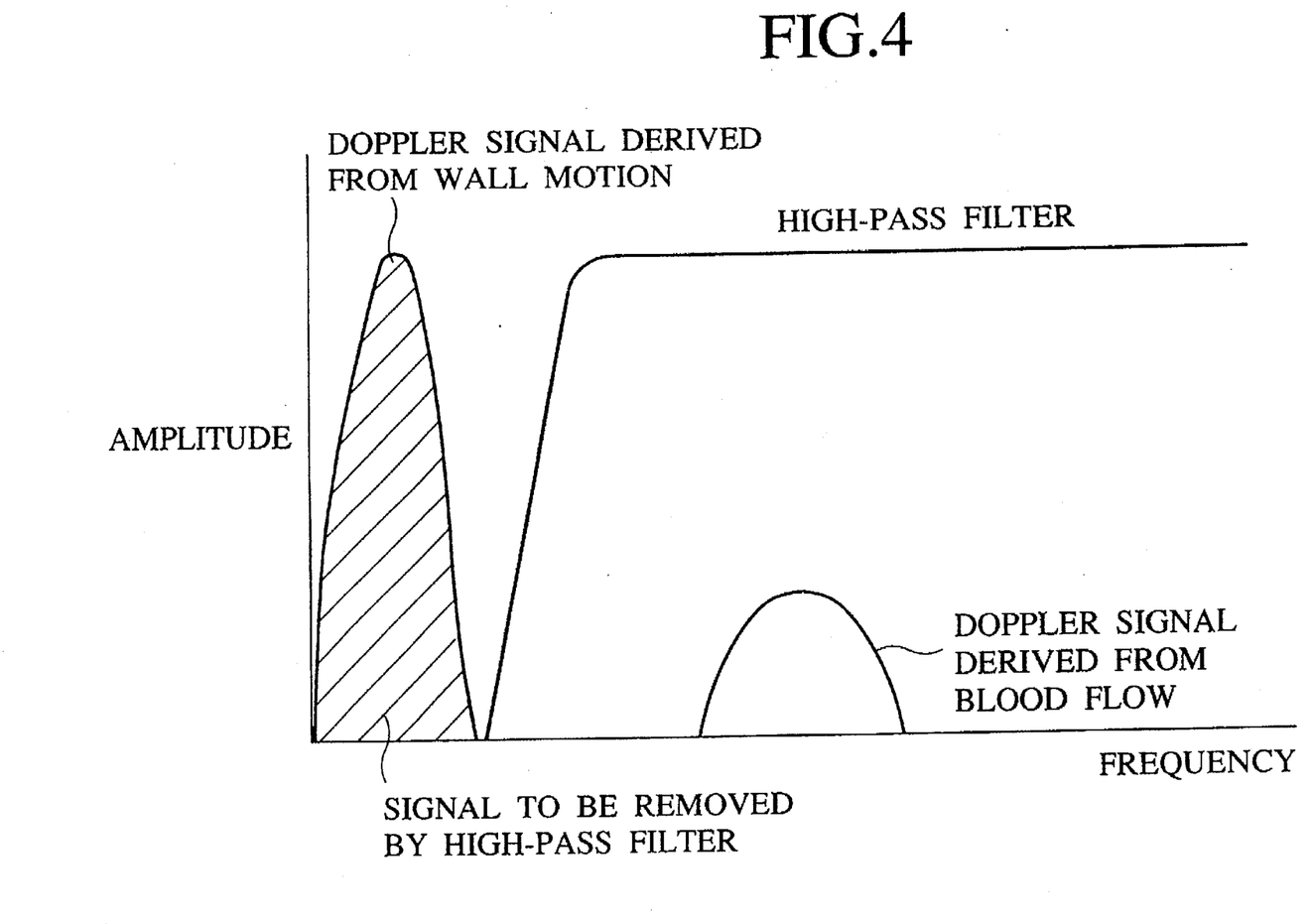
FIG. 4 is a diagram illustrating a method of extracting Doppler signals being derived from blood flow.
Figure 5:
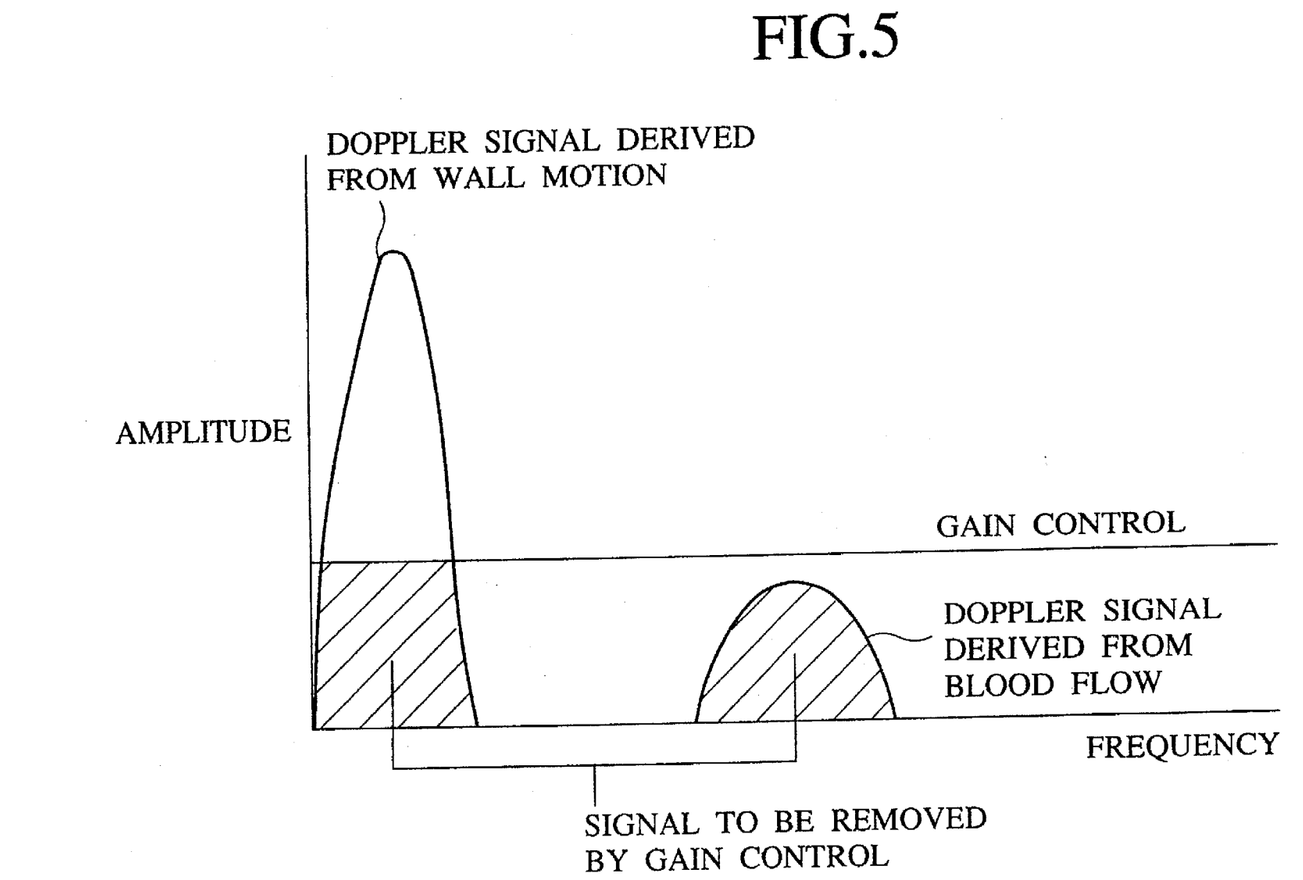
FIG. 5 is a diagram illustrating a method of extracting Doppler signals being derived from wall motion.

As shown in FIGS. 4 and 5, since the magnitude of motion velocities is in the order of "cardiac muscle<cardiac valve<blood flow", components of tissue motion velocity are distributed in the low frequency range of the echo signal and have a large amplitude (signal level). As a result, if appropriate values are allocated to the range and the coefficient for calculation of autocorrelation, the autocorrelator 22 and the velocity calculator 23 may extract tissue motion velocity information (Tissue Doppler Imaging =TDI) from the echo signals which are not passed through the high-pass filter portion 21, i.e., the echo signals which are passed through only the level controller 26b, as shown in FIG. 5. As stated earlier, information of tissue motion velocity obtained in the former half of one scanning are stored in predetermined pages of the frame memory in the DSC portion 25.

On the other hand, components of blood flow velocity are distributed in the high frequency range of the echo signal. Therefore, unnecessary frequency components caused by cardiac muscle, cardiac wall, and cardiac valve motion, for example, are removed by the high-pass filter portion 21 from the Doppler signal which being subjected to the phase detection, as shown in FIG. 4, and on the contrary blood flow components are passed through the high-pass filter portion 21.

Figures 3C, 3D, 3E:
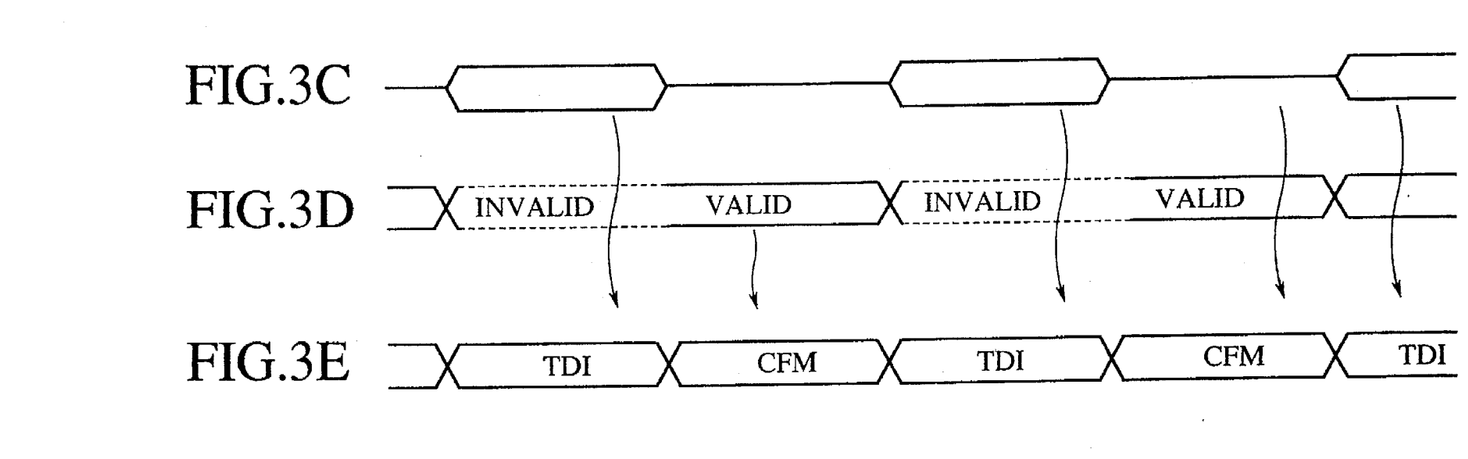

The reason why process of the echo signals being passed through the high-pass filter portion 21 is executed in the latter half of the process associated with one scanning line will now be explained hereinbelow. Because of transient response of the filter, the echo signals being passed through the high-pass filter portion 21 includes frequency components improper to signal processing at the beginning of the scanning (FIG. 3D). In other words, the echo signals based on the wall motion signals are included at the beginning of the scanning as it is, without being filtered. For this reason, it is in the latter half of one scanning that the echo signal being passed through the high-pass filter portion 21 is supplied to both the autocorrelator 22 and the velocity calculator 23. As a result, unnecessary frequency components are not included in the echo signals being passed through the high-pass filter portion 21, and therefore calculation of autocorrelation and velocity are executed based on necessary or effective frequency components. Thus, tissue motion velocity and blood flow velocity can be derived quickly. Information of blood flow velocity (CFM: Color Flow Mapping) thus obtained in the latter half of the scanning are stored in pages in the frame memory of the DSC portion 25, which are different from pages in the frame memory to be used for storing tissue motion velocity.

As discussed before, analysis of tissue motion velocity has been conducted in the former half of the process assigned to one scanning line while analysis of blood flow velocity has been conducted in the latter half thereof. These results are stored independently in different pages of the frame memory of the DSC portion 25 (FIG. 3E). Next, velocity data as for blood flow velocity and tissue motion velocity are read from the DSC portion 25, then converted into color display data while changing hue by the coloring circuit 24, and then output to the memory synthesizing portion 18.

The B-mode ultrasonic image and CDI images of blood flow velocity/tissue motion velocity and, if necessary, electro-cardiogram information are superposed by the memory synthesizing portion 18 and then displayed on the screen of the monitor 19.

As stated above, in the ultrasonic diagnostic equipment in FIG. 1, the Doppler signals obtained by phase-detecting the echo signals are switched by the signal selector 27 within the process associated with one scanning line so as to calculate autocorrelation and velocity of the Doppler signals which being passed through the high-pass filter portion 21 and autocorrelation and velocity of the Doppler signals which being not passed through the high-pass filter portion 21 respectively during different intervals of time of the process, so that tissue motion velocity and blood flow velocity may be analyzed simultaneously within every process associated with one scanning line of the ultrasonic pulses. Besides, tissue motion velocity and blood flow velocity derived from simultaneous analysis by the process associated with one scanning line may be read from the DSC portion 25 simultaneously to display on the screen of the monitor 19. Therefore, since tissue motion velocity and blood flow velocity may be evaluated simultaneously, a relation between movement of wall motion and movement of circulation of the blood may be evaluated more precisely and quantitatively if the ultrasonic diagnostic equipment of the present invention is used to diagnose cardiopathy, for example.

Moreover, since the autocorrelator 22 and the velocity calculator 23 calculates both autocorrelation and velocity in common by switching signal paths to them by virtue of the signal selector 27, there is little difference in a scale or size of the circuits between the equipment of the present invention and the conventional one and therefore the configuration of the equipment may be simplified. In addition, blood flow velocity may be detected with precision being identical to that in the conventional equipment.

Further, upon displaying the B-mode image and the CDI image concurrently, the B-mode image and the CDI image may be displayed selectively according to luminance of the B-mode image if these images are superposed on the same pixels. Therefore, even if the images are superposed, clear displaying of the monitor may be achieved. By changing hue of color according to blood flow velocity information and tissue motion velocity information, these information may be discriminated from each other even if these information are displayed concurrently.

With the above description, according to the embodiment of the present invention, both blood flow velocity and tissue motion velocity may be analyzed within the process assigned to one scanning based on the Doppler signals and may be simultaneously displayed apparently. Therefore, conditions of region of interest can be grasped readily and thus diagnosis can be pronounced more precisely.

According to the embodiment of the present invention, calculation of autocorrelation and velocity can be executed by the autocorrelator 22 and the velocity calculator 23 by virtue of switching the output signal of the high-pass filter portion 21 and the output signal of the level controller 26b by the signal selector 27. Thereby, tissue motion velocity and blood flow velocity may be derived respectively from low frequency components and high frequency components of the Doppler signals every process concerning to one scanning line. If tissue motion velocity and blood flow velocity which have thus been derived by simultaneous analysis every process assigned to one scanning line are stored in different pages of the frame memory and then output simultaneously, they may be displayed simultaneously.

According to the embodiment of the present invention, since autocorrelation and velocity as for the Doppler signals being passed through the high-pass filter portion are calculated in the latter half of the process concerning to one scanning line, calculations may be implemented without influence of unnecessary frequency components which are included in the former half of the process concerning to one scanning line. Instead, since autocorrelation and velocity as for the Doppler signals from the level controller 26b, i.e., the Doppler signals derived from tissue motion, are calculated in the former half of the process concerning to one scanning line, tissue motion velocity and blood flow velocity may be obtained quickly in the end.

According to the embodiment of the present invention, blood flow velocity and tissue motion velocity may be displayed distinguishably by displaying blood flow velocity and tissue motion velocity concurrently in different hue of color on the screen of the monitor 19.

According to the embodiment of the present invention, blood flow velocity and tissue motion velocity may be displayed distinguishably by causing the memory synthesizing portion 18 to display selectively blood flow velocity and tissue motion velocity on the screen of the monitor 19 according to luminance of the B-mode ultrasonic images.

According to the embodiment of the present invention, blood flow velocity and tissue motion velocity may be displayed distinguishably by causing the memory synthesizing portion 18 to display selectively blood flow velocity and tissue motion velocity on the screen of the monitor 19 according to the Doppler signals.

It should be understood that many modifications and adaptations of the invention will become apparent to those skilled in the art and it is intended to encompass such obvious modifications and changes in the scope of the claims appended hereto.

What is claimed is:

1. An ultrasonic diagnostic apparatus comprising:

a transducer for transmitting an ultrasonic beam into a subject and receiving an ultrasonic echo reflected from inside said subject and converting said received ultrasonic echo into electric echo signals;

an ultrasonic beam controller providing the ultrasonic beam along a given direction that is also the direction along which the ultrasonic echo reflected from inside the subject is received, said ultrasonic beam being provided and said reflected echo being received within a predetermined time period prior to providing a new ultrasonic beam in a different direction;

a B-mode ultrasonic image processing portion producing B-mode ultrasonic image data from said electric echo signals converted by said transducer;

a Doppler signal phase detecting portion having an input receiving said electric echo signals supplied from said transducer and functioning to detect and provide Doppler signals as an output;

a Doppler signal analyzer responsive to said Doppler signals to determine both blood flow velocity data and tissue motion velocity data within said predetermined time period;

a display control portion receiving said blood velocity data and said tissue motion velocity data along with B-mode ultrasonic image data and providing first display data as a combination of B-mode ultrasonic data with blood flow velocity data and second display data as a combination of B-mode ultrasonic data with tissue motion velocity data; and a display controlled by said display control portion to display said first display data and said second display data together.

2. An ultrasonic diagnostic apparatus as claimed in claim 1, wherein said Doppler signal analyzer determines said blood flow velocity data and said tissue motion velocity data in a time-division manner within the predetermined time period.

3. An ultrasonic diagnostic apparatus as claimed in claim 2, wherein said Doppler signal analyzer determines said tissue motion velocity data in a first portion of the predetermined period of time and determines said blood flow velocity data in a second portion of the predetermined period of time.

4. An ultrasonic diagnostic apparatus as claimed in claim 2, wherein said Doppler signal analyzer further comprises:

a discriminating portion discriminating input Doppler signals containing tissue motion data from input Doppler signals containing blood flow data and providing an output of Doppler signals that contain tissue motion data or blood flow data; and a velocity calculating portion calculating said blood flow velocity data or said tissue motion velocity data based on the output Doppler signals received from said discriminating portion.

5. An ultrasonic diagnostic apparatus as claimed in claim 4, wherein said discriminating portion further comprises:

a controller having a first portion permitting passage of Doppler signals having a level indicative of said blood flow data and a second portion blocking passage of said Doppler signals of a level indicative of said blood flow data but not blocking passage of said Doppler signals having a level indicative of tissue motion data;

a filter portion receiving said Doppler signals passed by said first portion to output a filtered output signal after removing low frequency components from said Doppler signals; and a signal selecting portion having a switching part selectively receiving said filtered output signal from said filter portion or an output signal from said second portion and providing the filtered output signal or the output signal from the second portion as the signals from the discriminating portion.

6. An ultrasonic diagnostic apparatus as claimed in claim 5, wherein said velocity portion further comprises:

an autocorrelation calculating portion receiving the signals from the discriminating portion to calculate an autocorrelation frequency distribution of the signals received from the discriminating portion; and a velocity calculating portion calculating said blood flow velocity data or said tissue motion velocity data based on autocorrelation calculation results output from said autocorrelation calculating portion.

7. An ultrasonic diagnostic apparatus as claimed in claim 6, further comprising:

a controller controlling selection of output Doppler signals from said discriminating portion by said signal selecting portion so as to selectively connect an output signal from said second level controlling portion for said first portion of said predetermined time period and then an output signal from said filter portion for said second portion of said predetermined period of time, said controller also providing both range and coefficient data for the autocorrelation calculation for the output signal of said second level controlling means and range and coefficient data for the autocorrelation calculation for the output signal of said high frequency filtering means to said autocorrelation calculating means and to said velocity calculating portion when a corresponding output signal is selected.

8. An ultrasonic diagnostic apparatus as claimed in claim 4, wherein said Doppler signal analyzer further comprises:

a digital scan converting and storage portion controller converting outputs received from the velocity calculating portion into data having a standard format for viewing and storing the format converted calculated velocity data relating to said blood flow velocity and said tissue motion velocity in a memory, and outputting of both the format converted calculated blood flow velocity data and the format converted calculated tissue motion velocity data from the memory simultaneously.

9. An ultrasonic diagnostic apparatus as claimed in claim 8, wherein said Doppler signal analyzer further comprises;

a coloring circuit which receives and converts said format converted calculated blood flow velocity data and said format converted calculated tissue motion velocity data into color display data.

10. An ultrasonic diagnostic apparatus as claimed in claim 9, wherein said coloring circuit further converts said format converted calculated blood flow velocity data and said format converted calculated tissue motion velocity data into color display data having different hue according to respective magnitudes of said blood flow velocity data and said tissue motion velocity data.

11. An ultrasonic diagnostic apparatus as claimed in claim 8, wherein said Doppler signal analyzer further comprises:

a display data converting circuit which converts said format converted calculated blood flow velocity data into color display data while said display data converting circuit converts said format converted calculated tissue motion velocity data into gray display data.

12. An ultrasonic diagnostic apparatus as claimed in claim 8, wherein said Doppler signal analyzer further comprises:

a display converting circuit which converts said format converted calculated blood flow velocity data into gray display data while said display correcting circuit converts said format converted calculated tissue motion velocity data into color display data.

13. An ultrasonic diagnostic apparatus as claimed in claim 1, wherein said display control portion further comprises:

a memory synthesizing portion superposing said B-mode ultrasonic image data with said blood flow velocity data to form said second display data and superposing B-mode ultrasonic image data with said tissue motion velocity data to form said first display data, said memory synthesizing portion further storing resultant superposed data.

14. An ultrasonic diagnostic apparatus as claimed in claim 13, wherein said memory synthesizing portion includes a controller for selectively controlling the storage of the resultant superposed data based upon the amplitude of said Doppler signal.

15. An ultrasonic diagnostic apparatus as claimed in claim 14, wherein said memory portion controller selectively provides said second display data for storage if said intensity of said Doppler signal is greater than or equal to a certain threshold value, and selectively provides said first display data for storage if said intensity of said Doppler signal is less than said certain threshold value.

16. An ultrasonic diagnostic apparatus as claimed in claim 13, wherein said controller included in said memory portion controls the storage of first display data or the second display data based upon luminance of said B-mode ultrasonic image data.

17. An ultrasonic diagnostic apparatus as claimed in claim 16, wherein said controller included in said memory selectively controls storage of said first display data if luminance of said B-mode ultrasonic image data is greater than or equal to a certain threshold value, and selectively controls storage of said second display data if said luminance of said B-mode ultrasonic image data is less than said certain threshold value.

18. An ultrasonic diagnostic apparatus as claimed in claim 1, wherein said display displays information indicating said tissue motion velocity data and information indicating said blood flow velocity data.

19. An ultrasonic diagnostic apparatus as claimed in claim 18, wherein said display displays said first display data and said second display data together or in an alternative manner.

* * * * *